(12) United States Patent
Apert et al.

(10) Patent No.: US 8,940,325 B2
(45) Date of Patent: Jan. 27, 2015

(54) USE OF SYNTHETIC POLYSULPHATED OLIGOSACCHARIDES AS CLEANING AGENTS FOR A WOUND

(75) Inventors: Laurent Apert, Dijon (FR); Christelle Laurensou, Dijon (FR); Dominque Nicot, Dijon (FR)

(73) Assignee: Laboratories Urgo (FR)

( * ) Notice: Subject to any disclaimer, the term of this patent is extended or adjusted under 35 U.S.C. 154(b) by 154 days.

(21) Appl. No.: 13/577,546

(22) PCT Filed: Feb. 16, 2011

(86) PCT No.: PCT/FR2011/050329
§ 371 (c)(1),
(2), (4) Date: Oct. 16, 2012

(87) PCT Pub. No.: WO2011/101594
PCT Pub. Date: Aug. 25, 2011

(65) Prior Publication Data
US 2013/0034596 A1    Feb. 7, 2013

(30) Foreign Application Priority Data
Feb. 17, 2010   (FR) ...................................... 10 51142

(51) Int. Cl.
| | | |
|---|---|---|
| *A61K 31/7016* | (2006.01) | |
| *A61K 31/702* | (2006.01) | |
| *A61P 17/02* | (2006.01) | |
| *A61K 38/43* | (2006.01) | |
| *A61L 15/58* | (2006.01) | |
| *C07H 5/10* | (2006.01) | |
| *A61K 31/70* | (2006.01) | |
| *A61L 15/18* | (2006.01) | |
| *A61F 13/00* | (2006.01) | |
| *A61L 15/28* | (2006.01) | |
| *A61L 15/44* | (2006.01) | |
| *A61L 15/60* | (2006.01) | |

(52) U.S. Cl.
CPC ................. *A61L 15/18* (2013.01); *A61F 13/00* (2013.01); *A61K 31/7016* (2013.01); *A61K 31/702* (2013.01); *A61L 15/28* (2013.01); *A61L 15/44* (2013.01); *A61L 15/60* (2013.01); *A61L 2300/232* (2013.01); *A61L 2300/404* (2013.01); *A61L 2300/41* (2013.01); *A61L 2300/45* (2013.01)
USPC .............. 424/445; 424/94.1; 514/23; 514/53; 514/61; 536/122

(58) Field of Classification Search
None
See application file for complete search history.

(56) References Cited

U.S. PATENT DOCUMENTS

| | | |
|---|---|---|
| 4,912,093 A | 3/1990 | Michaeli |
| 5,246,708 A | 9/1993 | von Borstel et al. |
| 5,916,880 A * | 6/1999 | Bar-Shalom et al. ........... 514/53 |
| 2004/0028739 A1 * | 2/2004 | Rippon et al. ................. 424/486 |
| 2006/0149182 A1 * | 7/2006 | Cullen et al. .................... 602/49 |
| 2007/0037776 A1 | 2/2007 | Richardson et al. |
| 2007/0059348 A1 * | 3/2007 | Friis et al. ..................... 424/445 |
| 2008/0299147 A1 | 12/2008 | Dillon et al. |

FOREIGN PATENT DOCUMENTS

| | | |
|---|---|---|
| EP | 230023 | 7/1987 |
| EP | 1764104 | 3/2007 |
| WO | 88/09347 | 12/1988 |
| WO | 94/00476 | 1/1994 |
| WO | 95/14483 | 6/1995 |
| WO | 95/34313 | 12/1995 |
| WO | 99/18974 | 4/1999 |
| WO | 2004062674 | 7/2004 |

OTHER PUBLICATIONS

International Search Report for PCT/FR2011/050329.

* cited by examiner

*Primary Examiner* — Robert A Wax
*Assistant Examiner* — Randeep Singh
(74) *Attorney, Agent, or Firm* — Caesar, Rivise, Bernstein, Cohen & Pokotilow, Ltd.

(57) ABSTRACT

The present invention relates to the use of at least one compound selected among the synthetic polysulphated oligosaccharides having 1 to 4 ose units and to the salts and complexes thereof as cleaning agents for a wound. The invention can be used in particular for preparing bandages intended for cleaning wounds.

35 Claims, No Drawings

USE OF SYNTHETIC POLYSULPHATED OLIGOSACCHARIDES AS CLEANING AGENTS FOR A WOUND

The present invention relates to the use of at least one compound selected from synthetic polysulfated oligosaccharides having 1 to 4 monosaccharide units, the salts and complexes thereof, as a cleaning agent.

More precisely, the present invention relates to the use of at least one such compound as an agent for degradation of the fibrin matrices that are part of the composition of fibrinous tissue. Notably, the present invention relates to the preparation of a composition intended to be used in the context of assisted cleaning.

Wound healing is a natural biological phenomenon, human and animal tissues being capable of repairing localized lesions by their inherent processes of repair and regeneration.

The natural healing of a wound takes place in three successive phases, each of these phases being characterized by specific cellular activities that cause the repair process to proceed according to precise chronological sequences: the cleaning phase, the granulation phase and the epithelialization phase.

Immediately after injury, the body reacts by implementing vascular and inflammatory phenomena in order to prevent any risk of hemorrhage and to protect the wound against the risks of infection.

These phenomena lead to formation of a fibrin-based matrix, which will contribute to stopping hemorrhage. This matrix also provides rough, temporary closure of the wound.

In order to initiate the next step of granulation, the body organizes in parallel the degradation of this fibrin matrix to make room for the extracellular matrix synthesized by the fibroblasts, which are the principal actors of the granulation phase. It is mainly this phase of removal of the fibrin matrix and the various kinds of debris present in the wound that is meant by the term "cleaning".

The cleaning phase is essential to the healing process. Its implementation and the speed with which it takes place are decisive for the success and rapidity of the healing process.

However, the capacities of natural cleaning may be insufficient when the injury is a major one or when the patient has concomitant disorders, such as venous disorders or diabetes. Thus, in these cases, one observes a cleaning phase which is significantly prolonged, leading to chronic wounds that are difficult to treat, for example leg ulcers.

Wounds are divided into two main types:
Wounds that have plaques of black tissues of varying hardness, commonly denoted by the term "necrotic tissues";
Wounds that have tissues that are soft and yellowish, commonly denoted by the term "fibrinous tissue" or "yellow fibrin".

In the case of wounds for which the natural cleaning process is insufficient, such as chronic wounds, it is necessary to remove the necrotic and/or fibrinous tissues. The removal of these necrotic and fibrinous tissues, which can be achieved by various techniques, is commonly denoted by the term "assisted cleaning", as opposed to natural cleaning.

Depending on the technique used, assisted cleaning can be described as mechanical or surgical cleaning, enzymatic cleaning, autolytic cleaning or biological cleaning.

The objective of assisted cleaning is to clean the wound, by removing the necrotic and/or fibrinous tissues that give rise to the risks of infection and can be a source of pain or of unpleasant odors, while preserving the maximum amount of healthy tissues present in the wound.

However, none of the cleaning techniques currently used is optimal and all of these techniques have many drawbacks.

Surgical or mechanical cleaning is a rapid technique that consists of cutting away the necrotic and/or fibrinous tissues, either using a lancet, forceps, scissors or a Brock curette, or by means of sophisticated apparatus using water jets under pressure or laser excision. This technique is performed at the patient's bed or in the surgical environment depending on the severity of the wound.

However, this technique is often painful and can lead to bleeding and sometimes even a hemorrhage. In such a case it represents a further trauma for the patient. It also commonly requires prior analgesic medication, which increases the treatment time.

Enzymatic cleaning is carried out by means of proteolytic enzymes such as streptokinase, trypsin or collagenase.

However, the use of these enzymes is far from optimal. In fact, these enzymes can be inactivated by local use of antiseptics and their activity can be limited by serum inhibitors that are present in the exudates from the wound. Moreover, some of these enzymes have very short half-lives and must be replenished frequently. These enzymes can, moreover, cause painful sensations during their application, reactions of sensitization or allergy, or may even create local erythema.

In the case of biological cleaning, also called maggot therapy, degradation of necrotic and/or fibrinous tissues is achieved by means of fly larvae that feed exclusively on dead tissues.

This technique also has several drawbacks, such as intense local pruritus, a certain degree of inflammation and a local burning sensation. Moreover, this technique is contraindicated in patients with clotting disorders or whose wounds are poorly vascularized or close to vital organs or large vessels. Finally, although very effective, the use of biological cleaning also encounters difficulties or psychological inhibition for the patient who sees or feels the presence of larvae in his or her wound.

Autolytic cleaning consists of placing absorbent dressings based on gelling fibers on the wound, which, by creating a moist environment, promote the natural cleansing role of the macrophages and polynuclear neutrophils while allowing softening of the fibrinous tissue and absorption of debris. Such a dressing, based on carboxymethylcellulose, is for example marketed by the company CONVATEC under the name AQUACEL®.

However, their action is slow and insufficient for removing large amounts of fibrinous tissue. It is therefore necessary to supplement autolytic cleaning with another technique, which is very often mechanical cleaning.

As compounds are available that can accelerate or promote the other phases of the healing process, it would therefore be desirable to have compounds or mixtures of compounds that are free from allergizing substances such as enzymes, which would make it possible to degrade necrotic and/or fibrinous tissues so as to optimize this cleaning phase.

The use of such compounds would in fact make it possible:
on the one hand, not to resort to techniques that are traumatizing physically or psychologically such as mechanical cleaning or maggot therapy; and
on the other hand, to optimize autolytic cleaning by incorporating these compounds in absorbent dressings, thus supplying a product allowing the degradation of necrotic and/or fibrinous tissues and absorption of the latter in a single step.

In this context, the present invention aims to solve the novel technical problem consisting of supplying said compounds that permit wound cleaning by degradation of the fibrin matrices that make up the necrotic tissues and/or fibrinous tissues.

It was discovered, quite surprisingly and unexpectedly, that synthetic polysulfated oligosaccharides having 1 to 4 monosaccharide units, the salts and complexes thereof, and in particular the potassium salt of sucrose octasulfate, make it possible to degrade fibrin matrices and can therefore be useful as cleaning agents.

Thus, according to a first aspect, the present invention relates to a composition comprising at least one compound selected from synthetic polysulfated oligosaccharides having 1 to 4 monosaccharide units, the salts and complexes thereof, for use as a wound cleaning agent.

The oligosaccharides that can be used in the context of the present invention are synthetic polymers formed from 1 to 4 monosaccharide units, and preferably from 1 or 2 monosaccharide units, generally bound to one another by an alpha or beta glycosidic bond. In other words, they are mono-, di-, tri- or tetrasaccharides, and preferably mono- or disaccharides.

There is no particular limitation regarding the nature of the monosaccharide units of these polysaccharides. Preferably, they will be pentoses or hexoses.

As examples of monosaccharide, we may mention glucose, galactose or mannose.

As examples of disaccharide, we may mention maltose, lactose, sucrose or trehalose.

As an example of trisaccharide, we may mention melezitose.

As an example of tetrasaccharide, we may mention stachyose.

Preferably, the oligosaccharide is a disaccharide, more preferably sucrose.

The expression "polysulfated oligosaccharide" denotes herein an oligosaccharide of which at least two, and preferably all the hydroxyl groups of each monosaccharide have been substituted with a sulfate group.

Preferably, the polysulfated oligosaccharide is sucrose octasulfate.

The polysulfated oligosaccharides used in the context of the present invention can be in the form of salts or complexes.

As examples of salts, we may mention the alkali metal salts such as the salt of sodium, of calcium or of potassium; a silver salt; or an amino acid salt.

As examples of complexes, we may mention hydroxyaluminum complexes.

In the context of the present invention, compounds that are particularly preferred are as follows:
    the potassium salt of octasulfated sucrose;
    the silver salt of octasulfated sucrose;
    the hydroxyaluminum complex of sucrose octasulfate commonly called sucralfate.

The potassium salt of sucrose octasulfate has been known for 25 years for treating wounds during the granulation phase owing to its action on fibroblasts. This action is described for example in patent applications EP 230 023, WO 89/05645 or WO 98/22114. As stated in these documents, this compound is used after carrying out assisted wound cleaning and therefore after removing the necrotic and/or fibrinous tissues (see EP 230 023, page 8, lines 10 to 15 and example 18; page 33, lines 28 to 30; see WO 89/05645, page 25, lines 8 and 9; and page 16, lines 25 to 28; see WO 98/22114, page 17, lines 18 to 20). Therefore it is used on a clean, cleansed wound.

In international patent application WO 89/05645 (see page 7 lines 13 to 24), it is stated that the polysulfated polysaccharides such as sucralfate are inhibitors of proteases, notably the hyaluronidases, which are enzymes capable of degrading hyaluronic acid and glycosaminoglycans.

It is therefore even more surprising that these compounds can find application in cleaning as the proteases are enzymes which, during the natural cleaning phase, can promote the degradation of damaged tissues. Inhibition of them therefore runs counter to good wound cleaning.

Although the mechanism by which the compounds used in the context of the present invention act is unknown at present, it has been demonstrated that they are capable of degrading a fibrin matrix reconstituted in vitro and this property was verified on samples taken from fibrinous tissues in vivo.

In general, these compounds can be used alone or as a mixture of two or more of them, or in combination with one or more other active substance(s) for inducing or accelerating healing or that may have a favorable role in wound treatment. Preferably, these compounds will be used with active substances that are of greater interest during the cleaning phase. Among these active substances, we may mention as examples, in particular:
    bactericidal or bacteriostatic agents (chlorhexidine, silver salts or complexes, zinc salts or copper salts, metronidazole, neomycin) for preventing or treating the risks of infections which are among the dangerous possible complications with necrosed tissues;
    local anesthetics (lidocaine);
    anti-inflammatories such as nonsteroidal anti-inflammatories (NSAIDs) (ibuprofen, ketoprofen, diclofenac), cyclooxygenase-2 inhibitors (celecoxib, rofecoxib) for relieving the pain that often accompanies these wounds;
    corticoids.

Of course, the compounds used in the context of the present invention can also be used with one or more other compound(s) that are known to have an action in the cleaning phase, for example:
    enzymes (which would thus make it possible to use the latter at lower concentrations and avoid their problem of sensitization);
    urea.

The compounds used in the context of the present invention can be employed simultaneously or successively with another active substance during the cleaning phase depending on the nature (infection, level of necrosis, painful wound) or the development (level of fibrinous tissue) of the wound to be cleaned.

In the context of their use as cleaning agents, the compounds used in the context of the present invention will be employed in a pharmaceutical formulation, for example a gel, a solution, an emulsion, a cream, granules or capsules of variable size in the range from nano- or micrometer to millimeter, which will allow their application directly on the wound. If they are used as a mixture of two or more of them or in combination with one or more other active substances, these compounds can be incorporated in the same pharmaceutical formulation or in separate pharmaceutical formulations.

Alternatively, and preferably, the compounds used in the context of the present invention or a pharmaceutical formulation containing them will be integrated in a dressing.

"Dressing" means herein all types of dressings used for treating wounds, and preferably absorbent dressings, as the wounds to be treated during the cleaning phase are often very exudative.

For simplicity, the expression "cleaning agent according to the invention" will be used hereinafter to designate any compound or mixture of compounds selected from the oligosaccharides of the sulfates described above and whose use is claimed here.

The cleaning agent according to the invention or a pharmaceutical formulation containing it can be incorporated in any element of the structure of a dressing.

Preferably and in order to promote rapid action, this compound (or a pharmaceutical formulation containing it) will be incorporated in the layer of the dressing that comes in contact with the wound or will be deposited on the surface of the dressing that comes in contact with the wound.

Such techniques for deposition are well known by a person skilled in the art and some are described for example in patent application WO 2006/007844.

Advantageously, the cleaning agent according to the invention (or a pharmaceutical formulation containing it) can thus be deposited, continuously or discontinuously, on the surface that is intended to come in contact with the wound:
- either in liquid form, for example by evaporation of a solution or suspension containing it;
- or in solid form, for example by sifting of a powder containing it.

The layer or surface coming in contact with the wound can for example consists of an absorbent material such as an absorbent hydrophilic polyurethane foam; a textile material such as a compress, for example a nonwoven, a film, an adhesive material—absorbent or nonabsorbent; an adherent or nonadherent interface structure.

In general, the pharmaceutical form or the structure of the dressing will be adapted to obtain a specific release profile, rapid or delayed, depending on requirements, of the cleaning agent according to the invention.

Of course, the amount of cleaning agent according to the invention used in the pharmaceutical formulation or in the dressing will be adapted in relation to the required kinetics as well as the specific constraints associated with its nature, solubility, heat resistance, etc.

Thus, for use in a pharmaceutical formulation, the cleaning agent according to the invention can be incorporated in an amount between 0.1 and 50 wt. % relative to the total weight of the formulation.

In the context of its use in an element of a dressing, the cleaning agent according to the invention will be incorporated in an amount such that the amount of this cleaning agent released in the exudates from the wound is between 0.001 g/l and 50 g/l, and preferably between 0.001 and 10 g/l.

In a preferred embodiment, the cleaning agent according to the invention will be incorporated in an absorbent dressing based on gelling fibers, for example the product AQUACEL® marketed by the company CONVATEC. This will thus optimize the cleaning power of this type of product that is already used in the context of autolytic cleaning.

According to a further preferred variant, the cleaning agent according to the invention will be incorporated in a dressing consisting of a nonwoven based on superabsorbent fibers that gel in contact with wound exudates. Such fibers are marketed for example by the company TOYOBO Co Ltd under the name LANSEAL® F.

In order to reinforce the integrity of these nonwovens after absorption, these superabsorbent fibers can be combined, for example by needling or thermal bonding, with thermal-bonding fibers such as two-component fibers consisting of a polyester core and a polyethylene shell.

Non-woven dressings that can be used in this context are described for example in international patent application WO 2007/085391.

Very often, during placement of these dressings, the care personnel hold the latter in place by means of a bandage or cover them with a secondary element such as a second absorbent dressing or even a tight bandage. It is therefore useful if the dressing remains fixed on the wound so that the care personnel have their hands free for placing these secondary elements.

In the context of the present invention, a nonwoven will therefore preferably be used, such as those mentioned above, in which the surface coming in contact with the wound is covered with a discontinuous layer of adhesive. The latter can be for example in the form of fibers of adhesives, a perforated adhesive layer, a discontinuous layer of adhesive in the form of strips or a thread or any other discontinuous geometric pattern.

In general, any type of adhesive commonly used in dressings can be used for this purpose.

So as not to adversely affect the healthy tissues or the edges of the wound, notably when removing the dressing, an adhesive will be preferred that has the property of adhering to the skin without adhering to the wound.

As examples of such an adhesive, we may thus mention adhesives based on elastomers of silicone or of polyurethane, such as gels of silicone or of polyurethane and hydrocolloid adhesives.

Such hydrocolloid adhesives consist of an elastomeric matrix based on one or more elastomers selected from poly (styrene-olefin-styrene) block polymers in combination with one or more compounds selected from plasticizers, such as mineral oils, tackifying resins and, if necessary, antioxidants, in which a, preferably small, amount of hydrocolloid (3 to 20 wt. %) is incorporated, for example sodium carboxymethylcellulose or superabsorbent polymers such as the products marketed under the name LUQUASORB® by the company BASF.

The formulation of these hydrocolloid adhesives is well known by a person skilled in the art and is described for example in patent applications FR 2 392 076 and FR 2 495 473.

The use of a thread of adhesive on the nonwoven makes it possible, particularly advantageously, to decrease or avoid the risk of small fibrils of textile material coming in contact with the wound and becoming attached to the tissues, thus causing pain during removal, or even presenting an obstacle to the wound healing process. Furthermore, it provides better control of the flow of liquid in or on the textile material and can reduce or eliminate the risks of "gel blocking", resulting from the use of superabsorbent fibers which in fact limit the absorption capacity of the nonwoven.

According to a preferred embodiment of the present invention, the cleaning agent according to the invention will be incorporated in said adhesive at a concentration compatible with its solubility and its heat resistance.

Based on these criteria, the cleaning agent according to the invention will preferably be used in an amount between 1 and 15 wt %, and more preferably between 5 and 10 wt. %, relative to the total weight of the adhesive.

If we wish to increase the absorption of this nonwoven dressing, we can combine the latter with an additional absorbent layer, and preferably an absorbent layer that does not gel, such as in particular an absorbent hydrophilic foam, preferably a hydrophilic polyurethane foam having an absorption capacity greater than that of the nonwoven.

Such foams, and their method of manufacture, notably from mixtures based on prepolymer, water, surfactant etc., are well known to a person skilled in the art and are described for example in the following patent applications: WO 96/16099, WO 94/29361, WO 93/04101, EP 420 515, EP 392 788, EP 299 122, and WO 2004/074343.

The nonwoven and the foam will be combined by techniques that are well known to a person skilled in the art, for example by hot calendering using a hot-melt powder based on TPU/polycaprolactone polymers. This technique is commonly used for bonding nonwovens together that are intended for the medical market.

Finally, this foam or the nonwoven (when the latter is used alone) can be covered with a support to protect the wound from the outside environment. This support can be of larger size than the other layers and can be made adhesive continuously or discontinuously on its face coming in contact with the wound in order to optimize holding of the dressing in place during use, in particular if the wound is located on areas of the body that are not flat.

This support and its adhesive will preferably be impermeable to fluids but very permeable to water vapor in order to permit optimal management of the exudates absorbed by the dressing and avoid problems of maceration.

Supports of this kind are well known by a person skilled in the art and consist for example of films that can breathe and are impermeable such as polyurethane films, foam/film or nonwoven/film complexes.

According to another aspect, the present invention relates to a method of treating wounds that comprises the use of a composition according to the invention comprising at least one compound selected from synthetic polysulfated oligosaccharides having 1 to 4 monosaccharide units, salts and complexes thereof.

In the context of this method of treatment, this composition is applied to the wound by any suitable means and in particular by means of a dressing such as those described above.

The activity of the cleaning agent according to the invention has been demonstrated in various conditions:
on the one hand, on models of fibrin matrices prepared in vitro; and
on the other hand, on fibrinous tissue taken from wounds.

The tests that were carried out, and which will be described in detail below, have thus demonstrated the ability of this compound to degrade fibrin matrices and fibrinous tissue. These tests also demonstrated, in the in vitro model, the ability of a dressing to degrade a fibrin matrix, this dressing being usable in the context of autolytic cleaning and consisting of a nonwoven based on gelling fibers having, on its surface intended to come in contact with the wound, a thread of hydrocolloid adhesive incorporating the cleaning agent according to the invention.

The results obtained showed:
on the one hand, the advantage of the cleaning agent according to the invention in the context of wound cleaning; and
on the other hand, the advantage of using the cleaning agent according to the invention, in the context of autolytic cleaning, where its incorporation in an absorbent dressing, commonly used in this technique, makes it possible to obtain an optimal product, which combines both the properties of absorption of debris and the action of degradation of fibrinous tissue.

EXAMPLE 1

Demonstration of the Effect of the Potassium Salt of Sucrose Octasulfate on the Degradation of the Fibrin Matrix Prepared In Vitro 1. Production of Fibrin Matrices In Vitro The fibrin matrices were prepared according to Brown's protocol described in the work "Fibroblast migration in fibrin gel matrices" Am J. Pathol, 1993, 142: 273-283.

The components and the procedure employed are as follows:
The following were dissolved at 37° C.:
5 ml of an aqueous solution comprising 50 millimoles of Hepes (Sigma-Aldrich Catalog)
15 mg of human plasma fibrinogen (Sigma-Aldrich Catalog)
5 millimoles of $CaCl_2$.
50 µl of thrombin, 100 NIH of human plasma (Sigma-Aldrich Catalog) were added to the solution thus prepared.
The reaction mixture was mixed, put in a 15-ml tube (or a Petri dish of 60 mm diameter) and then left to incubate at 37° C.

During the first 24 hours of incubation at 37° C., a fibrin matrix which has roughly the appearance of a gel was seen to appear.

After 24 hours, observation of this fibrin matrix under a microscope showed the formation of a homogeneous filamentary network.

2. Demonstration of the Effect of the Potassium Salt of Sucrose Octasulfate on Degradation of the Fibrin Matrix 24 h after the start of formation of the fibrin matrix in the aforementioned 15-ml tube, a solution of potassium salt of sucrose octasulfate was added in an amount of 1 volume of solution of this compound to 5 volumes of the fibrinogen/thrombin mixture used for preparing the fibrin matrix.

In parallel, a control solution was prepared free from the test compound with phosphate-buffered saline (PBS).

The degradation of the fibrin matrix was monitored visually over the next 24 and 48 hours.

The resultant observations were classified in 3 levels:
No degradation: the matrix remains unchanged.
Partial degradation: disintegration of the matrix.
Total degradation: the matrix disappears.

3. Determination of PDFs:

In order to quantify and verify that the observations made do indeed correspond to degradation of the fibrin matrix, the products of degradation of fibrin (PDFs) were determined 24 hours or 48 hours after adding the solutions of the test compound.

This determination was performed according to a conventional technique using a plasma PDF assay kit with the reference 00540 marketed by the company Diagnostica Stago.

Thus, 20 µl of supernatant was taken from the 15-ml tube that was placed at the center of the red ring of a plate of the PDF assay kit. 20 µl of suspension of latex particles was added. After stirring, the analysis was carried out.

By correlating the visual results and the measurements of PDFs, the results obtained were quantified:
if the value of the PDFs, expressed in µg/ml, is below 5, there is no degradation of the fibrin matrix,
if the value of the PDFs, expressed in µg/ml, is between 5 and 20, there is partial degradation of the fibrin matrix,
if the value of the PDFs, expressed in µg/ml, is greater than 20, there is total degradation of the fibrin matrix, which disappears.

4. Tests with the Potassium Salt of Sucrose Octasulfate:

An aqueous solution of potassium salt of sucrose octasulfate was prepared at 10 g/l.

This solution was tested according to the protocol described above and the PDFs were measured 48 hours after adding the solution to the fibrin matrix.

To assess the relevance of the results, a solution of PBS was tested as negative control and, as positive control, the product Accuzyme®, which contains papain as proteolytic enzyme, together with urea, which is used in the context of enzymatic cleaning.

By measuring the PDFs, the following results were obtained:
PBS: below 5 µg/ml
Accuzyme®: above 20 µg/ml
Solution of potassium salt of sucrose octasulfate at 10 g/l: between 5 and 20 µg/ml.

This demonstrated the effectiveness of the potassium salt of sucrose octasulfate, which led to partial degradation of the fibrin matrix.

EXAMPLE 2

Demonstration of the Effect of the Potassium Salt of Sucrose Octasulfate on Fibrinous Tissue Withdrawn In Vivo The same solution of potassium salt of sucrose octasulfate was tested on fibrinous tissue withdrawn in vivo.

For this test, a sample of fibrinous tissue from a leg ulcer of venous origin of 5 $mm^2$ was put in a 15-ml tube maintained at 37° C.

After 24 hours, 1 ml of solution of potassium salt of sucrose octasulfate was deposited on this sample.

Once again, a negative control was prepared with PBS and a positive control with Accuzyme®.

The PDFs were assayed 48 hours after introduction of the active substance or of the control.

This experiment was repeated on 5 samples of fibrinous tissues obtained from the same patient.

Thus, it was found that the potassium salt of sucrose octasulfate led, in this test, to total degradation of the fibrin matrix, thus demonstrating its effectiveness.

Measurement of the PDFs confirmed this result, the values measured being as follows:
Accuzyme®: above 20 µg/ml
PBS: below 5 µg/ml
Potassium salt of sucrose octasulfate: above 20 µg/ml These results therefore confirm, on fibrinous tissue taken in vivo, the results obtained on the model in vitro, the measured level of effectiveness being better here than on the fibrin matrix model in vitro.

EXAMPLE 3

Demonstration of the Effect of the Potassium Salt of Sucrose Octasulfate Incorporated in an Absorbent Dressing on Degradation of the Fibrin Matrix Prepared In Vitro 1. Preparation of an Absorbent Dressing Containing the Potassium Salt of Sucrose Octasulfate Using thermal bonding, a nonwoven of 180 g/$m^2$ was prepared that can be used as an absorbent dressing in the context of autolytic cleaning by means of LANSEAL® F superabsorbent fibers marketed by the company TOYOBOCOLTD and of two-component thermal-bonding polyester/polyethylene fibers in a ratio 70% (superabsorbent fibers)/30% (thermal-bonding fibers).

In addition, a hydrocolloid adhesive was prepared containing the potassium salt of sucrose octasulfate by mixing in an MEL G-40 mixer.

The composition of this adhesive, expressed in percentage by weight relative to the total weight of the adhesive, was as follows:
Mineral oil marketed by the company Shell under the name Ondina®917: 32.8%
Sodium salt of carboxymethylcellulose (hydrocolloid) marketed by the company AQUALON under the name CMC Blanose® 7H4XF: 14%
Potassium salt of sucrose octasulfate marketed by the company EUTICALS: 7.5%
Block copolymer of poly(styrene-ethylene-butylene) (elastomer) marketed by the company KRATON under the name KRATON® G 1654: 6%
Antioxidant marketed under the name IRGANOX® 1010 by the company CIBA SPECIALTY CHEMICALS: 0.12%
Copolymer of salt of 2-methyl-2[(1-oxo-2-propenyl)amino]-1-propanesulfonic acid and of 2-hydroxyethyl ester of propenoic acid (salting-out agent) marketed by the company SEPPIC under the name SEPINOV® EMT 10: 5%
Tackifying resin marketed by the company EXXON CHEMICALS under the name ESCOREZ® 5380: 35%.

The various constituents were added at a temperature between 100 and 110° C. with stirring, so as to obtain a homogeneous mixture.

More precisely, first the mineral oil, the hydrocolloid, the potassium salt of sucrose octasulfate and the elastomer were added, and then the antioxidant and the salting-out agent and finally the tackifying resin.

This adhesive was coated discontinuously in a configuration in the form of a thread on the previously prepared nonwoven.

2. Tests of the Dressings on the In Vitro Fibrin Matrix Model

The dressing containing the potassium salt of sucrose octasulfate and the autolytic dressing marketed by the company CONVATEC under the name AQUACEL® were then compared.

For this purpose, fibrin matrices were prepared in Petri dishes of 60 mm diameter following the protocol described above.

After 24 hours, a 20 mm diameter sample of each of the 2 dressings described above was placed, at room temperature, on the fibrin matrix.

The dressings were removed 24 hours after being placed, and the fibrin matrix was observed visually.

It was found that a more or less pronounced hole had formed in the fibrin matrix, under the area corresponding to the sample of the dressing containing the potassium salt of sucrose octasulfate. In contrast, the fibrin matrix remained intact for the sample of the AQUACEL® product.

This experiment therefore confirmed the effectiveness of the potassium salt of sucrose octasulfate for degradation of fibrin matrices and the advantage of incorporating it in a dressing usable in the context of autolytic cleaning.

The invention claimed is:

1. A composition comprising at least one compound selected from synthetic polysulfated oligosaccharides having 1 to 4 monosaccharide units, salts and complexes thereof, for use as a wound cleaning agent wherein said composition is applied to an external skin wound in a cleaning phase of said skin wound, wherein fibrin matrix is degraded by applying said composition.

2. The composition of claim 1, wherein the compound is selected from synthetic polysulfated oligosaccharides having 1 or 2 monosaccharide units, and salts and complexes thereof.

3. The composition of claim 2 wherein the compound is selected from pentoses and hexoses, and salts and complexes thereof.

4. The composition as claimed in claim 1 wherein the compound is selected from the group consisting of a potassium salt of sucrose octasulfate, a silver salt of sucrose octasulfate and a sucralfate.

5. The composition of claim 1 wherein the compound is combined with one or more other active substances for inducing or accelerating healing in wound treatment.

6. The composition of claim 5 wherein the active substance is selected from the group consisting of bactericidal or bacteriostatic agents, local anesthetics, anti-inflammatories, and corticoids.

7. The composition of claim 5, wherein the compound is combined with one or more additional wound cleaning agents.

8. The composition of claim 1 wherein the compound is used in a pharmaceutically acceptable formulation permitting application directly on a wound.

9. The composition of claim 8 wherein the compound used as a wound cleaning agent is present in an amount between 0.1 and 50 weight %, relative to the total weight of the formulation.

10. The composition of claim 8 wherein the formulation is a gel, a solution, an emulsion, a cream, a granule or a capsule.

11. The composition of claim 1 wherein the compound is integrated with an element of a dressing in an amount such that the amount of the compound released in wound exudates is between 0.001 g/l and 50 g/l.

12. The composition of claim 11 wherein the compound is integrated with an element of a dressing in an amount such that the amount of the compound released in wound exudates is between 0.001 and 10 g/l.

13. The composition of claim 8 wherein the pharmaceutical formulation is integrated with an element of a dressing in an amount such that the amount of the compound released in wound exudates is between 0.001 g/l and 50 g/l.

14. The composition of claim 13, wherein the dressing comprises absorbent fibers.

15. The composition of claim 13 wherein the dressing comprises a nonwoven material consisting of superabsorbent fibers combined with thermal-bonding fibers, wherein the surface of the nonwoven material comes in contact with the wound and is covered with a discontinuous layer of adhesive.

16. The composition of claim 15 wherein the adhesive is a hydrocolloid adhesive and the polysulfated oligosaccharide is incorporated in said adhesive.

17. The composition of claim 16 wherein the polysulfated oligosaccharide is incorporated in said adhesive in an amount between 1 and 15 wt. % relative to the weight of the adhesive.

18. The composition of claim 16 wherein the polysulfated oligosaccharide is incorporated in said adhesive in an amount between 5 and 10 wt. % relative to the weight of the adhesive.

19. A method of treatment of an external skin wound comprising applying a composition to the external skin wound in a cleaning phase of said skin wound, wherein fibrin matrix is degraded by applying said composition in said cleaning phase, said composition comprising at least one compound selected from synthetic polysulfated oligosaccharides having 1 to 4 monosaccharide units, salts and complexes thereof.

20. The method of treatment of claim 19 additionally comprising the step of selecting the at least one compound of the composition to be from synthetic polysulfated oligosaccharides having 1 or 2 monosaccharide units, and salts and complexes thereof.

21. The method of treatment of claim 20 additionally comprising the step of selecting the at least one compound of the composition to be from pentoses and hexoses, and salts and complexes thereof.

22. The method of treatment of claim 19 additionally comprising the step of selecting the at least one compound of the composition from the group consisting of a potassium salt of sucrose octasulfate, a silver salt of sucrose octasulfate and a sucralfate.

23. The method of treatment of claim 19 additionally comprising the step of combining the at least one compound of the composition with one or more other active substances for inducing or accelerating healing in wound treatment.

24. The method of treatment of claim 23 additionally comprising the step of selecting the active substance from the group consisting of bactericidal or bacteriostatic agents, local anesthetics, anti-inflammatories, and corticoids.

25. The method of treatment of claim 23 additionally comprising the step of combining the at least one compound with one or more additional wound cleaning agents.

26. The method of treatment of claim 19 additionally comprising the step of selecting the at least one compound to be one that is used in a pharmaceutically acceptable formulation permitting application directly on a wound.

27. The method of treatment of claim 26 additionally comprising the step of selecting the at least one compound used as a wound cleaning agent to be present in an amount between 0.1 and 50 weight %, relative to the total weight of the formulation.

28. The method of treatment of claim 26 wherein the pharmaceutically acceptable formulation is a gel, a solution, an emulsion, a cream, a granule or a capsule.

29. The method of treatment of claim 19 additionally comprising the step of selecting the at least compound to be integrated with an element of a dressing in an amount such that the amount of the compound released in wound exudates is between 0.001 g/l and 50 g/l.

30. The method of treatment of claim 26 additionally comprising the step of selecting the pharmaceutical formulation to be integrated with an element of a dressing in an amount such that the amount of the compound released in wound exudates is between 0.001 g/l and 50 g/l.

31. The method of treatment of claim 30, additionally comprising selecting the dressing to comprise absorbent fibers.

32. The method of treatment of claim 30 additionally comprising selecting the dressing to comprise a nonwoven material consisting of superabsorbent fibers combined with thermal-bonding fibers, wherein the surface of the nonwoven material comes in contact with the wound and is covered with a discontinuous layer of adhesive.

33. The method of treatment of claim 32 additionally comprising the step of selecting the adhesive to be a hydrocolloid adhesive and the polysulfated oligosaccharide is incorporated in said adhesive.

34. The method of treatment of claim 33 additionally comprising the step of selecting the polysulfated oligosaccharide to be incorporated in said adhesive in an amount between 1 and 15 wt. % relative to the weight of the adhesive.

35. The method of treatment of claim 33 additionally comprising the step of selecting the polysulfated oligosaccharide to be incorporated in said adhesive in an amount between 5 and 10 wt. % relative to the weight of the adhesive.

* * * * *